US006667163B2

(12) United States Patent
Mandala et al.

(10) Patent No.: US 6,667,163 B2
(45) Date of Patent: Dec. 23, 2003

(54) POLYNUCLEOTIDE SEQUENCES ENCODING MOUSE SPHINGOSINE-1-PHOSPHATE PHOSPHATASE

(75) Inventors: Suzanne M. Mandala, Scotch Plains, NJ (US); Rosemary A. Thornton, Warren, NJ (US)

(73) Assignee: Merck & Co., Inc., Rahway, NJ (US)

( * ) Notice: Subject to any disclaimer, the term of this patent is extended or adjusted under 35 U.S.C. 154(b) by 107 days.

(21) Appl. No.: 09/778,171

(22) Filed: Feb. 7, 2001

(65) Prior Publication Data

US 2002/0012984 A1 Jan. 31, 2002

Related U.S. Application Data

(60) Provisional application No. 60/180,534, filed on Feb. 7, 2000.

(51) Int. Cl.$^7$ .......................... C12P 21/04; C12N 15/00; C12N 15/09; C12N 15/63; C12N 15/70
(52) U.S. Cl. ................... 435/70.1; 435/320.1; 435/325; 536/23.1; 536/23.2; 536/23.5
(58) Field of Search ............................ 536/23.1, 23.2, 536/23.5; 435/320.1, 325, 70.1; 514/44

(56) References Cited

PUBLICATIONS

GenBank Accession No., AA691033, submitted Dec. 16, 1997).
Nagashima, et al., "Primary Structure and Transcription of Genes Encoding B870 and Photosynthetic Reaction Center Apoproteins from *Rubrivivax gelatinosus*" J. Biol Chem 269, No. 4, 1994, p. 2477–2484.
Tate, et al., "Molecular Cloning of Magnesium–Independent Type 2 Phosphatidic Acid Phosphates from Airway Smooth Muscle" Cell Signal 11, No. 7, 1999, p. 515–522.
Brindley, et al., "Analysis of Ceramide 1–phosphate and Sphingosine–1–phosphate Phosphatase Activities" Methods in Enzymology 311, 1999, p. 233–244.
Capecchi, et al, "Targeted Gene Replacement" Scientific American, 1994 p. 52–59.
Lee. et al. "Vascular Endothelial Cell Adherens Junction Assembly and Morphogenesis Induced by Sphingosine–1–Phosphate". Cell 99, 1999, p. 301–312.
Saba. et al. "The BST1 Gene of *Saccharomyces cerevisiae* Is the Sphingosine–1–phosphate Lyase". J. Biol. Chem. 272, 1997, p. 26087–26090.
Mandala. et al. "Sphingoid base 1–phosphate phosphatase: A key regulator of sphingolipid metabolism and stress response". Proc. Nat. Acad. Sci. USA 95, 1998, p. 150–155.
Goetzl. et al. Diversity of cellular receptors and functions for the lysophospholipid growth factors lysophosphatidic acid and sphingosine 1–phosphate. FASEB J. 12, 1998, p. 1589–1598.

Toke. et al. "Isolation and Characterization of the *Saccharomyces cerevisiae* DPP1 Gene Encoding Diacylglycerol Pyrophosphate Phosphatase". J. Biol. Chem. 273, 1998, p. 3278–3284.
Toke. et al. "Isolation Characterization of the *Saccharomyces cerevisiae* LPP1 Gene encoding a Mg2+–independent Phosphatidate Phosphatase". J. Biol. Chem. 273, 1998, p. 14331–14338.
Zhou. et al. "Identification of the First Mammalian Sphingosine Phosphate Lyase Gene and Its Functional Expression in Yeast". Biochem. Biophys. Res. Commun. 242, 1998, p. 502–507.
Mao. et al. "Identification and Characterization of *Saccaromyces cerevisiae* Dihydrosphingosine–1–phosphate Phosphatase". J. Biol Chem. 272, 1997, p. 28690–28694.
Olivera. et al. "Sphingosine Kinase Expression Increases Intracellular Sphingosine–1–phosphate and Promotes Cell Growth and Survival". J. Cell Biol. 147, 1999, p. 545–548.
Van Brocklyn. et al. "Dual Actions of Spimgosine–1–Phosphate: Extracellular through the Gi– coupled Receptor Edg–1 and Intracellular to Regulate Proliferation and Survival". J. Cell Biol. 142, 1998, p. 229–240.
Edsall. et al. "Involvement of Sphingosine 1–Phosphate in Nerve Growth Factor– Mediated Neuronal Survival and Differentiation". J. Neurosci 17, 1997, p. 6952–6960.
Rani. et al. "Divergence in Signal Transduction Pathways of Platelet–derived Growth Factor (PDGF) and Epidermal Growth Factor (EGF) Receptors". J. Biol. Chem. 272, 1997, p. 10777–10783.
Kohama. et al. "Molecular Cloning and Functional Characterization of Murine Sphingosine Kinase". J. Biol. Chem. 273, 1998, p. 23722–23728.
Olivera. et al. "Purification and Characterization of Rat Kidney Sphingosine Kinase". J. Biol. Chem. 273, 1998, p. 12576–12583.
Cuvillier. et al. "Sphingosine 1–Phosphate Inhibits Activation of Caspases that Cleave Poly (ADP–ribose) Polymerase and Lamins during Fas– and Ceramide–mediated Apoptosis in Jurkat T Lymphocytes". J. Biol. Chem. 273, 1998, p. 2910–2916.
Nagiec. et al. "The LCB4 (YOR171c) and LCB5 (YLR260w) Genes of Saccharomyces Encode Sphingoid Long Chain Base Kinases". J. Biol. Chem. 273, 1998, p. 19437–19442.

(List continued on next page.)

*Primary Examiner*—Peter Paras
(74) *Attorney, Agent, or Firm*—Michael D. Yablonsky; Jack L. Tribble

(57) ABSTRACT

The present invention provides polynucleotides and polypeptides of a murine sphingosine-1-phosphate phosphatase, referred to herein as mSPP1. The polynucleotides and polypeptides are used to further provide expression vectors, host cells comprising the vectors, probes and primers, antibodies against the mSPP1 protein and polypeptides thereof, assays for the presence or expression of mSPP1 and assays for the identification of compounds that interact with mSPP1.

6 Claims, 4 Drawing Sheets

OTHER PUBLICATIONS

Melendez. et al. FcγRI Coupling to Phospholipase D Initiates Sphingosine Kinase–mediated Calcium Mobilization and Vesicular Trafficking. J. Biol. Chem. 273, 1998, p. 9393–9402.

Van Koppen. et al. "Activation of a High Affinity Gi Protein–coupled Plasma Membrane Receptor by Sphingosine–1–phosphate". J. Biol. Chem. 271, 1996, p. 2082–2087.

Van Brocklyn. et al. "Sphingosine 1–Phosphate–induced Cell Rounding and Neurite Retraction Are Mediated by the G Protein–coupled Receptor H218". J. Biol. Chem. 274, 1999, p. 4626–4632.

Wang. et al. "Sphingosine 1–Phosphate Stimulates Cell Migration through a Gi–coupled Cell Surface Receptor". J. Biol. Chem. 274, 1999, p. 35343–35350.

Hisano. et al. Hemostasis, Thrombosis, and Vascular Biology "Induction and Suppression of Endothelial Cell Apoptosis by Sphingolipids: A Possible In Vitro Model for Cell–Cell Interactions Between Platelets and Endothelial Cells". Blood 93, 1999, p. 4293–4299.

Brindley. et al. "Mammalian Lipid Phosphate Phopsphohydrolases". J. Biol. Chem. 273, 1998, p. 24281–24284.

Xia. et al. "Tumor necrosis factor–a induces adhesion molecule expression through the sphingosine kinase pathway". Proc. Natl. Acad. Sci. USA 95, 1998, p. 14196–14201.

M.J. Evans. et al. "Establishment in culture of pluripotential cells from mouse embryos". Nature 292: 1981, p. 154–156.

Mattie. et al. "Sphingosine–1–phosphate, a Putative Second Messenger, Mobilizes Calcium from Internal Stores via an Inositol Trisphosphate–independent Pathway". J. Biol. Chem. 269, 1994, p. 3181–3188.

Kleuser. et al. "1a,25–Dihydroxyvitamin D3 Inhibits Programmed Cell Death in HL–60 Cells by Activation of Sphingosine Kinase". Cancer Res. 58, 1998, p. 1817–1824.

Devereux J. et al. "A comprehensive set of sequence analysis programs for the VAX". Nucleic Acids Research 12(1): 1984, p. 387.

Atschul, S.F. et al. "Basic Local Alignment Search Tool". J. Molec Biol 215: 1990, p. 403.

Spiegel, S. "Sphingosine 1–phosphate: a prototype of a new class of second messengers". J. Leukoc. Biol. 65, 1999, p. 341–244.

Robertson. et al. "T–cell receptor: gamma gene product surfaces". Nature 322: 1986, p. 445–448.

Cuvillier. et al. "Suppression of ceramide–mediated programmed cell death by sphingosine–1–phosphate". Nature 381, 1996, p. 800–803.

Bradley. et al. "Formation of germ–line chimaeras from embryo–derived teratocarcinoma cell lines". Nature 309: 1984, p. 255–258.

Choi. et al. "Calcium mobilization via sphingosine kinase in signalling by the Fc&RI antigen receptor". Nature 380, 1996. p. 634–636.

Olivera. et al. "Sphingosine–1–phosphate as second messenger in cell proliferation induced by PDGF and FCS mitogens". Nature 365, 1993, p. 557–560.

Stukey. et al. "Identification of a novel phosphatase sequence motif". Protein Sci. 6, 1997, p. 469–472.

R. Jaenisch. "Transgenic Animals". Science 240: 1988, p. 1468–1474.

Gossler. et al. "Transgenesis by means of blastocyst–derived embryonic stem cell lines". Proc. Natl. Acad. Sci. USA 83: 1986, p. 9065–9069.

Meyer Zu Herindorf. et al. "Sphingosine kinase–mediated Ca2+ signalling by G–protein–coupled receptors". EMBO J. 17, 1998, p. 2830–2837.

Yamamura. et al. "Sphingosine 1–Phosphate Regulates Melanoma Cell Motility through a Receptor–Coupled Extracellular Action and in a Pertussis Toxin–Insensitive Manner". Biochemistry 36, 1997, p. 10751–10759.

Mao. et al. "The dihydrosphingosine–1–phosphate phosphatases of *Saccharomyces cerevisiae* are important regulators of cell proliferation and heat stress responses". Biochem. J. 342, 1999, p. 667–675.

De Ceuster. et al. "Identification and subcellular localization of sphinganine–phosphatases in rat liver". Biochem. J. 311, 1995, p. 139–146.

Le Stunff. et al. "Characterization of Murine Sphingosine–1–phosphate Phosphohydrolase". The Journal of Biological Chemistry, vol. 277, No. 11, 2002, p. 8920–8927.

Postma. et al. "Sphingosine–1–phosphate rapidly induces Rho–dependent neurite retraction" action through a specific cell surface receptor. EMBO J. 15, 1996, p. 2388–2392.

Skrypek. et al. "Analysis of Phosphorylated Sphingolipid Long–Chain Bases Reveals Potential Roles in Heat Stress and Growth Control in saccharomyces". J. Bacteriol. 181, 1999, p. 1134–1140.

Gottlieb. et al. "The DPL1 Gene Is Involved in Mediating the Response to Nutrient Deprivation in *Saccharomyces cerevisiae*". Mol. Cell Biol. Res. Commun. 1, 1999, p. 66–71.

Carillo, H. et al. "The Multiple Sequence Alignment Problem In Biology". Siam J. Applied Math 48: 1998, p. 1073.

Perez. et al. "Apoptosis–associated signaling pathways are requred for chemotherapy–mediated female germ cell destruction". Nature Med. 3, 1997. p. 1228–1232.

Mandala. et al. "Molecular Cloning and Charachterization of a lipid phosphohydro;ase that degrades sphingosine–1–phosphate and induces cell death". Proc. Natl. Acad. Sci. USA, vol. 97 No. 14, 2000, p. 7859–7864.

Mandala. et al. "Sphingoid base 1–phosphate phosphatase: A Key regulator of sphingolipid metabolism and stress response". Proc. Natl. Acad. Sci. USA, vol. 95 1998, p. 150–155.

Veldhoven. et al. "Sphinganine 1–phosphate metabolism in cultured skin fibroblasts: evidence for the existence of a sphingosine phosphatase". Biochem. J. 299, 1994, p. 597–601.

De Custer. et al. "Identification and subcellular localization of sphinganine–phosphatases in rat liver". Biochem. J. 311, 1995, p. 139–146.

FIG. 1 mSPP1 Polynucleotide Sequence

```
   1 gccagtgcca agctaaaatt aaccctcact aaagggaata agcttgcggc cgctgcggcc
  61 tgttggcgcg gtcgccggca gcctcgagcg agtcgagcta ggcaccgtgg cggctgtggc
 121 tggcgaggag cgcgtggccg gatcaattcc cgagtggccc gcgaccatgt ccctggggca
 181 gcggctggct ctgctggcca gccgtctgca ggagccgcag cgggtggcga gcttccagcg
 241 tctgtgtggg gtggaggtgc cgctcagcag cccggcggcg gacgaggatg cagagaccga
 301 ggttcgcgga gccccgggag aaccccggcg acggggacgg cagccgggcg ctgaggacag
 361 ccccgccaag gcggactgct gcggtgcccc gaacggcgtg cgcaacgggc tggcggccga
 421 gccgggcccg accgggcccc gccgcgcggg ctcgcagcgc cgcaactcgt gacgggcga
 481 ggagggcgag ctggtcaaag tgagcaactt gccgctctac tacctgttct gcctaggcac
 541 ggaactgggc aacgagctct tctacatctt attcttcccc ttctggatct ggaatctcga
 601 ccccctttgtg gccggaggc tggtgatcat ctgggtgctg gtcatgtacc tgggccagtg
 661 caccaaggac atcatccgct ggccacggcc ggcctcgccg cctgtcatca agctggaggt
 721 cttctacaac tcggaataca gcatgccctc cacgcatgcc atgtcaggca ccgccatccc
 781 catcgccatg ttcctgctca cctatggccg ctggcagtat cctcttatct acgggctgat
 841 tctcattccc tgctggagtt cactagtttg cctaagtaga atctacatgg gaatgcattc
 901 tatcctggat gtcattgctg gattcttgta taccatttta atcttaatta tcttctaccc
 961 attggtggac ctgattgaca acttcaacca aacttacaaa tatgcgccgc tcatcatcat
1021 cgggcttcac ttaattttgg gcatcttctc tttcacccttt gacacctgga gcacatcccg
1081 aggagacacg gctgagattc tgggaagtgg tgctgggatt gcatgtggct cacacgctgc
1141 ttataccctg ggcctatcct tagaaccttc tctgcacatg ttacccttag ctatccccc
1201 tcttactgta actctgtttg aaaagccat attacggatc gtcctaggaa tgctgcttgt
1261 actgttcgtg agggatatca tgaagaagat caccattcct ctagcctgta aactctccag
1321 tattccgtgt catgacattc gccaagcaag gcagcacatg gaagtggagc tgccataccg
1381 gtatattacc tacgggatgg ttgggttctc catcacgttt ttggtcccct atgtatttc
1441 ctttattggt atctcttgat ggaggaacac tgtttgttat aagaaaggag gctaccagct
1501 atatctaaag ctattctcta ggtaaaactt ggatcagagg cttctgcaag aatttgactt
1561 aaagaagtaa attctgcagc cagtgcattc tctcattgca caccagatgt tgttttacgt
1621 gggctgagct ctctcagtgc tgagaaatgg cgcgcccatt tagaatgttc accaaatgtt
1681 tggggagttc tgtgctgtta caaattgtag ttatatatac catatattaa ggcacacggt
1741 gtgcaaggt gtgtctagta tatattatat atacaactgt ttacctaaca acagtggggt
1801 gtattgaaaa aaatcagtaa caatatgcag ttgtgcccag gttttggaa ttaatgcagg
1861 catgttgagg cttctgcaag aatttgactt aaagaagtaa attctgcagc cagtgcattc
1921 tctcattgca caccagatgt tgttttacgt gggctgagct ctctcagtgc tgagaaatgg
1981 cgcgcccatt tagaatgttc accaaatgtt tggggagttc tgtgctgtta caaattgtag
2041 ttatatatac catatattaa ggcacacggt gtgcaaggt gtgtctagta tatattatat
2101 atacaactgt ttacctaaca acagtggggt gtattgaaaa aaatcagtaa caatatgcag
2161 ttgtgcccag gttttggaa ttaatgcagg catgttg    (SEQ ID NO:1)
```

FIG. 2 mSPP1b Polynucleotide Sequence

```
   1 atgggagaag agctgggcca ctgtgtccaa atgagaaaaa gtaatgagag gggcaaacgt
  61 ttcagagagc agagagtaca gagagctcag ggaaaggtat cacaccacac caaagaagag
 121 gaggagacaa gagtgagaca gatgagccaa ggctgggagg aaaaggagta tgggtactac
 181 ctgttctgct taggcacgga actgggcaac gagctcttct acatcttatt cttcccttc
 241 tggatctgga atctcgaccc ctttgtgggc cggaggctgg tgatcatctg ggtgctggtc
 301 atgtacctgg ccagtgcac caaggacatc atccgctggc cacggccggc ctcgccgcct
 361 gtcatcaagc tggaggtctt ctacaactcg aatacagca tgccctccac gcatgccatg
 421 tcaggcaccg ccatccccat cgccatgttc ctgctcacct atggccgctg gcagtatcct
 481 cttatctacg ggctgattct cattccctgc tggagttcac tagtttgcct aagtagaatc
 541 tacatgggaa tgcattctat cctggatgtc attgctggat tcttgtatac cattttaatc
 601 ttaattatct tctacccatt ggtggacctg attgacaact tcaaccaaac ttacaaatat
 661 gcgccgctca tcatcatcgg gcttcactta attttgggca tcttctcttt cacccttgac
 721 acctggagca catcccgagg agacacggct gagattctgg aagtggtgc tgggattgca
 781 tgtggctcac acgctgctta taccctgggc ctatccttag aaccttctct gcacatgtta
 841 cccttagcta tcccccctct tactgtaact ctgtttggaa aagccatatt acggatcgtc
 901 ctaggaatgc tgcttgtact gttcgtgagg gatatcatga agaagatcac cattcctcta
 961 gcctgtaaac tctccagtat tccgtgtcat gacattcgcc aagcaaggca gcacatggaa
1021 gtggagctgc cataccggta tattacctac gggatggttg ggttctccat cacgttttg
1081 gtcccctatg tatttccctt tattggtatc tcttga   (SEQ ID NO:2)
```

FIG. 3 mSPP1 Polypeptide

MSLGQRLALLASRLQEPQRVASFQRLCGVEVPLSSPAADEDAETEVRGAPGEPRRRGRQP
GAEDSPAKADCCGAPNGVRNGLAAEPGPTGPRRAGSQRRNSLTGEEGELVKVSNLPLYYL
FCLGTELGNELFYILFFPFWIWNLDPFVGRRLVIIWVLVMYLGQCTKDIIRWPRPASPPV
IKLEVFYNSEYSMPSTHAMSGTAIPIAMFLLTYGRWQYPLIYGLILIPCWSSLVCLSRIY
MGMHSILDVIAGFLYTILILIIFYPLVDLIDNFNQTYKYAPLIIIGLHLILGIFSFTLDT
WSTSRGDTAEILGSGAGIACGSHAAYTLGLSLEPSLHMLPLAIPPLTVTLFGKAILRIVL
GMLLVLFVRDIMKKITIPLACKLSSIPCHDIRQARQHMEVELPYRYITYGMVGFSITFLV
PYVFSFIGIS*

FIG. 4 mSPP1b Polypeptide

```
MGEELGHCVQMRKSNERGKRFREQRVQRAQGKVSHHTKEEEETRVRQMSQGWEEKEYGYY
LFCLGTELGNELFYILFFPFWIWNLDPFVGRRLVIIWVLVMYLGQCTKDIIRWPRPASPP
VIKLEVFYNSEYSMPSTHAMSGTAIPIAMFLLTYGRWQYPLIYGLILIPCWSSLVCLSRI
YMGMHSILDVIAGFLYTILILIIFYPLVDLIDNFNQTYKYAPLIIIGLHLILGIFSFTLD
TWSTSRGDTAEILGSGAGIACGSHAAYTLGLSLEPSLHMLPLAIPPLTVTLFGKAILRIV
LGMLLVLFVRDIMKKITIPLACKLSSIPCHDIRQARQHMEVELPYRYITYGMVGFSITFL
VPYVFSFIGIS*   (SEQ ID NO:4)
```

POLYNUCLEOTIDE SEQUENCES ENCODING MOUSE SPHINGOSINE-1-PHOSPHATE PHOSPHATASE

CROSS-REFERENCE TO RELATED APPLICATIONS

This application claims the benefit of U.S. Provisional Application No. 60/180,534 filed Feb. 7, 2000, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

The invention relates to mammalian sphingosine-1-phosphate phosphatase, polynucleotides encoding the enzyme and assays that measure the catabolism of sphingosine-1-phosphate by mammalian sphingosine-1-phosphate phosphatase.

BACKGROUND OF THE INVENTION

Sphingosine-1-phosphate (SPP) is a bioactive sphingolipid metabolite which regulates diverse biological processes (reviewed in (Goetzl, et al., (1998) *FASEB J.* 12, 1589–1598 and Spiegel, S. (1999) *J. Leukoc. Biol.* 65, 341–344.) Many of its actions are reported to be mediated by a family of specific cell surface G-protein coupled receptors (GPCR), known as EDG (endothelial differentiation genes) receptors. Binding of SPP to EDG-1 expressed on endothelial cells reportedly enhances survival (Hisano, et al., (1999) *Blood* 93, 4293–4299), chemotaxis and in vitro angiogenesis (Wang, et al., (1999) *J. Biol. Chem.* 274, 35343–35350) and adherens junction assembly leading to morphogenetic differentiation (Lee, et al., (1999) *Cell* 99, 301–312), whereas binding of SPP to EDG-5 and EDG-3 is reported to induce neurite retraction and soma rounding (Postma, et al., (1996) *EMBO J.* 15, 2388–2392 and Van Brocklyn, et al., (1999) *J. Biol. Chem.* 274, 4626–4632). Additional research indicates that SPP induces activation of $G_i$-gated inward rectifying $K^+$-channels in atrial myocytes (van Koppen, et al., (1996) *J. Biol. Chem.* 271, 2082–2087) and inhibits motility of melanoma cells (Yamamura, et al., (1997) *Biochemistry* 36, 10751–10759) through as yet uncharacterized GPCRs.

SPP is also described as performing important roles inside cells. In response to diverse external stimuli, sphingosine kinase, the enzyme that catalyzes the phosphorylation of sphingosine to SPP, is activated (Olivera, et al., (1993) *Nature* 365, 557–560; Choi, et al., (1996) *Nature* 380, 634–636; Melendez, et al., (1998) *J. Biol. Chem.* 273, 9393–9402; Xia, et al., (1998) *Proc. Natl. Acad. Sci. USA* 95, 14196–14201; Kleuser, et al., (1998) *Cancer Res.* 58, 1817–1824 and Meyer zu Heringdorf, et al., (1998) *EMBO J.* 17, 2830–2837). Intracellular SPP in turn mobilizes calcium from internal stores independently of $InsP_3$ (Meyer zu Heringdorf, et al., (1998) *EMBO J.* 17, 2830–2837 and Mattie, et al., (1994) *J. Biol. Chem.* 269, 3181–3188), as well as eliciting diverse signaling pathways leading to proliferation (Rani, et al., (1997) *J. Biol. Chem.* 272, 10777–10783 and Van Brocklyn, et al., (1998) *J. Cell Biol.* 142, 229–240.) and suppression of apoptosis (Cuvillier, et al., (1996) *Nature* 381, 800–803; Perez, et al., (1997) *Nature Med.* 3, 1228–1232; Edsall, et al., (1997) *J. Neurosci.* 17, 6952–6960; Cuvillier, et al., (1998) *J. Biol. Chem.* 273, 2910–2916).

Because of its dual function as a ligand and second messenger and its pivotal role in cell growth and survival, the synthesis and degradation of SPP is expected to be tightly regulated in a spatial-temporal manner. Until recently, however, little was known of the enzymes involved in SPP metabolism. A previous report described the purification of sphingosine kinase to apparent homogeneity from rat kidney (Olivera, et al., (1998) *J. Biol. Chem.* 273, 12576–12583). Subsequently the first mammalian sphingosine kinase was cloned from rat and characterized (Kohama, et al., (1998) *J. Biol. Chem.* 273, 23722–23728). The kinase is described as belonging to a novel, highly conserved gene family (Kohama, et al., (1998) *J. Biol. Chem.* 273, 23722–23728 and Nagiec, et al., (1998) *J. Biol. Chem.* 273, 19437–19442). Enforced expression of the sphingosine kinase markedly enhanced the proliferation and survival of cells, substantiating the importance of intracellularly generated SPP in cell fate decisions (Olivera, et al., (1999) *J. Cell Biol.* 147, 545–548).

SPP can be metabolized by two distinct pathways. In one pathway, SPP is catabolized via a microsomal pyridoxal phosphate-dependent lyase to palmitaldehyde and phosphoethanolamine, which can then be utilized for the biosynthesis of glycerolipids. In a second pathway, SPP is dephosphorylated by specific phosphatases to sphingosine (Spiegel, et al., (1996) *FASEB J.* 10, 1388–1397).

Genetic manipulation studies in yeast have demonstrated an important role for long-chain phosphorylated sphingoid bases in growth and survival of yeast after nutrient deprivation and heat stress (Mandala, et al., (1998) *Proc. Nat. Acad. Sci. USA* 95, 150–155; Gottlieb, et al., (1999) *Mol. Cell Biol. Res. Commun.* 1, 66–71; Mao, et al., (1999) *Biochem. J.* 342, 667–675 and Skrzypek, et al., (1999) *J. Bacteriol.* 181, 1134–1140) in a manner which is reminiscent of their effects on mammalian cells. Recently, the yeast genes encoding the lyase and phosphatase enzymes of these two catabolic pathways were identified in *S. cerevisiae* (Saba, et al. (1997) *J. Biol. Chem.* 272, 26087–26090; Mandala, et al., (1998) *Proc. Nat. Acad. Sci. USA* 95, 150–155 and Mao, et al., (1997) *J. Biol. Chem.* 272, 28690–28694). While the mammalian counterpart of the yeast SPP lyase has recently been identified (Zhou, et al., (1998) *Biochem. Biophys. Res. Commun.* 242, 502–507), a specific mammalian SPP phosphatase has not been previously reported.

The yeast SPP phosphatases encoded by LBP1 and LBP2 are members of Type 2 lipid phosphate phosphohydrolases, a family of magnesium independent, membrane-bound enzymes that share sequence conservation within three domains that are predicted to be involved in the coordination and hydrolysis of the phosphate moiety (Stukey, et al., (1997) *Protein Sci.* 6, 469–472). A search of the yeast genome for enzymes containing the three conserved domains revealed the presence of 4 genes encoding putative Type 2 lipid phosphatases. Two of these, DPP1 and LPP1, were shown to encode phosphatases with activity against phosphatidic acid (PA), lysophosphatidic acid (LPA), and diacylglycerol pyrophosphate (DGPP) (Toke, et al., (1998) *J. Biol. Chem.* 273, 14331–14338 and Toke, et al., (1998) *J. Biol. Chem.* 273, 3278–3284). In contrast, LBP1 (also known as YSR2 or LCB3) and LBP2 (YSR3), encode phosphatases with remarkable specificity for phosphorylated sphingoid bases and without activity towards glycerolipid substrates (Mandala, et al., (1998) *Proc. Nat. Acad. Sci. USA* 95, 150–155; Mao, et al., (1997) *J. Biol. Chem.* 272, 28690–28694 and Skrzypek, et al., (1999) *J. Bacteriol.* 181, 1134–1140).

The presence of a high affinity SPP phosphatase activity with enzymatic properties similar to yeast SPP phosphatases has been described in crude rat liver and cerebellum extracts (De Ceuster, et al., (1995) *Biochem. J.* 311, 139–146). Although three isoforms of Type 2 lipid phosphate phosphohydrolases, known as LPP1/PAP2a, LPP3/PAP2b, and LPP2/PAP2c, have been cloned from mammalian cells (reviewed in (Brindley, et al., (1998) *J. Biol. Chem.* 273, 24281–24284)), these gene products appear to have broad substrate specificity with similar efficiencies against PA, LPA, SPP, ceramide-1-P, and DGPP, when assayed in vitro in lipid/detergent micelles.

SUMMARY OF THE INVENTION

The present invention provides polynucleotides encoding a murine sphingosine-1-phosphate phosphatase (mSPP1), recombinant host cells containing mSPP1 polynucleotides, mSPP1 polypeptides, and methods of using the polynucleotides, polypeptides and host cells to conduct assays of sphingosine-1-phosphate phosphatase activity.

Polynucleotides and polypeptides of mammalian mSPP1, an enzyme involved in the catoblism of sphingosine-1-phosphate (SPP) are provided. The recombinant mSPP1 enzyme is catalytically active in the dephosphorylation of SPP. The enzyme is used in in vitro and whole cell assays to screen for compounds that alter the activity of the protein or interact with mSPP1 and, potentially, alter the expression of mSPP1. The invention includes the polynucleotides, proteins encoded by the polynucleotides, host cells expressing the recombinant enzyme and extracts prepared from host cells expressing the recombinant enzyme, probes and primers, and the use of these molecules in assays.

An aspect of this invention is a polynucleotide having a sequence encoding a mSPP1 protein, or a complementary sequence. In a particular embodiment the encoded protein has a sequence corresponding to SEQ ID NO:3. In other embodiments, the encoded protein can be a naturally occurring mutant or polymorphic form of the protein. In preferred embodiments the polynucleotide can be DNA, RNA or a mixture of both, and can be single or double stranded. In particular embodiments, the polynucelotide is comprised of natural, non-natural or modified nucleotides. In some embodiments, the internucleotide linkages are linkages that occur in nature. In other embodiments, the internucleotide linkages can be non-natural linkages or a mixture of natural and non-natural linkages. In a most preferred embodiment, the polynucleotide has the coding sequence contained in sequence SEQ ID NO:1.

An aspect of this invention is a polynucleotide having a sequence of at least about 25 contiguous nucleotides that is specific for a naturally occurring polynucleotide encoding a mSPP1 protein. In particular preferred embodiments, the polynucleotides of this aspect are useful as probes for the specific detection of the presence of a polynucleotide encoding a mSPP1 protein. In other particular embodiments, the polynucleotides of this aspect are useful as primers for use in nucleic acid amplification based assays for the specific detection of the presence of a polynucleotide encoding a mSPP1 protein. In preferred embodiments, the polynucleotides of this aspect can have additional components including, but not limited to, compounds, isotopes, proteins or sequences for the detection of the probe or primer.

An aspect of this invention is an expression vector including a polynucleotide encoding a mSPP1 protein, or a complementary sequence, and regulatory regions. In a particular embodiment the encoded protein has a sequence corresponding to SEQ ID NO:3. In particular embodiments, the vector can have any of a variety of regulatory regions known and used in the art as appropriate for the types of host cells the vector can be used in. In a most preferred embodiment, the vector has regulatory regions appropriate for the expression of the encoded protein in mammalian host cells. In other embodiments, the vector has regulatory regions appropriate for expression of the encoded protein in other eukaryotes, bacteria, yeasts, insect cells, cyanobacteria or actinomycetes. In some preferred embodiments the regulatory regions provide for inducible expression while in other preferred embodiments the regulatory regions provide for constitutive expression. Finally, according to this aspect, the expression vector can be derived from a plasmid, phage, virus or a combination thereof.

An aspect of this invention is host cell comprising an expression vector including a polynucleotide encoding a mSPP1 protein, or a complementary sequence, and regulatory regions. In a particular embodiment the encoded protein has a sequence corresponding to SEQ ID NO:3. In preferred embodiments, the host cell is a eukaryote, yeast, insect cell, gram-positive bacterium, cyanobacterium or actinomycete. In a most preferred embodiment, the host cell is a mammalian cell.

An aspect of this invention is a process for expressing a mSPP1 protein in a host cell. In this aspect a host cell is transformed or transfected with an expression vector including a polynucleotide encoding a mSPP1 protein, or a complementary sequence. According to this aspect, the host cell is cultured under conditions conducive to the expression of the encoded mSPP1 protein. In particular embodiments the expression is inducible or constitutive. In a particular embodiment the encoded protein has a sequence corresponding to SEQ ID NO:3.

Other aspects of this invention include polynucleotides, expression vectors, host cells and process that employ mSPP1b polynucleotides having the sequence of SEQ ID NO:2 or encoding the amino acid sequence of SEQ ID NO:4.

An aspect of this invention is a purified mSPP1 polypeptide having an amino acid sequence of SEQ ID NO:3 or the sequence of a naturally occurring mutant or polymorphic form of the protein such as the mSPP1b protein having the amino acid sequence of SEQ ID NO:4.

An aspect of this invention is a method of determining whether a candidate compound can alter the activity of a mSPP1 polypeptide. According to this aspect a polynucleotide encoding the polypeptide is used to construct an expression vector appropriate for a particular host cell. The host cell is transformed or transfected with the expression vector and cultured under conditions conducive to the expression of the mSPP1 polypeptide. Cells are disrupted and membranes are collected by centrifugation. The membranes, or mSPP1 polypeptide purified from the membranes, are contacted with the candidate. Finally, one measures the activity of the mSPP1 polypeptide in the presence of the candidate. If the activity is lower relative to the activity of the protein in the absence of the candidate, then the candidate is a inhibitor of the mSPP1 polypeptide. In preferred embodiments, the polynucleotide encodes a protein having an amino acid sequence of SEQ ID NO:2 or a naturally occurring mutant of polymorphic form thereof. In other preferred embodiments, the polynucleotide has the sequence of SEQ ID NO:1. In particular embodiments, the relative activity of mSPP1 is determined by comparing the activity of the mSPP1 in a host cell. In some embodiments, the host cell is contacted with the candidate and activity of mSPP1 protein is determined by measuring a cell phenotype that is dependent upon mSPP1 function. Finally, according to this aspect the relative activity can determined by comparison to a previously measured or expected activity value for the mSPP1 activity in the host under the conditions. However, in preferred embodiments, the relative activity is determined by measuring the activity of the mSPP1 in a control cell that was not contacted with a candidate compound. In particular embodiments, the host cell is a mammalian cell and the protein inhibited is the mSPP1 produced by the mammalian cell.

By "about" it is meant within 10% to 20% greater or lesser than particularly stated.

As used herein an "agonist" is a compound or molecule that interacts with and stimulates an activity of mSPP1.

As used herein an "antagonist" is a compound that interacts with mSPP1 and interferes with the interaction of mSPP1 and SPP.

As used herein an "inhibitor" is a compound that interacts with and inhibits or prevents mSPP1 from catalyzing the dephosphorylation of SPP by mSPP1.

As used herein a "modulator" is a compound that interacts with an aspect of cellular biochemistry to effect an increase or decrease in the amount of a polypeptide of mSPP1 present in, at the surface or in the periplasm of a cell, or in the surrounding serum or media. The change in amount of the mSPP1 polypeptide can be mediated by the effect of a modulator on the expression of the protein, e.g., the transcription, translation, post-translational processing, translocation or folding of the protein, or by affecting a component(s) of cellular biochemistry that directly or indirectly participates in the expression of the protein. Alternatively, a modulator can act by accelerating or decelerating the turnover of the protein either by direct interaction with the protein or by interacting with another component(s) of cellular biochemistry which directly or indirectly effects the change.

An aspect of this invention is a transgenic animal useful for the study of the tissue and temporal specific expression or activity of the mSPP1 gene in a non-human animal. The animal is also useful for studying the ability of a variety of compounds to act as agonists, antagonists or inhibitors of mSPP1 activity or expression in vivo or, by providing cells for culture or assays, in vitro. In an embodiment of this aspect of the invention, the animal is used in a method for the preparation of a further animal which lacks a functional endogenous mSPP1 gene. In another embodiment, the animal of this aspect is used in a method to prepare an animal which expresses a non-native mSPP1 gene in the absence of the expression of a endogenous gene. In particular embodiments the non-human animal is a mouse. In further embodiments the non-native mSPP1 gene is a wild-type mSPP1 gene or a mutant mSPP1 gene.

All of the references cited herein are incorporated by reference in their entirety as background material.

BRIEF DESCRIPTION OF THE DRAWINGS

FIG. 1 is the polynucleotide sequence of SEQ ID NO:1.
FIG. 2 is the polynucleotide sequence of SEQ ID NO:2.
FIG. 3 is the polypeptide sequence of SEQ ID NO:3.
FIG. 4 is the polypeptide sequence of SEQ ID NO:4.

DETAILED DESCRIPTION OF THE INVENTION

The present invention provides polynucleotides and polypeptides of a murine sphingosine-1-phosphate phosphatase, referred to herein as mSPP1. The polynucleotides and polypeptides are used to further provide expression vectors, host cells comprising the vectors, probes and primers, antibodies against the mSPP1 protein and polypeptides thereof, assays for the presence or expression of mSPP1 and assays for the identification of compounds that interact with mSPP1.

Sphingosine and sphingosine-1-phosphate (SPP) are interconvertible sphingolipid metabolites with opposing effects on cell growth and apoptosis. The mammalian homolog of yeast SPP-phosphatase, murine SPP phosphatase-1 (mSPP1) differs from yeast LPP phosphatases in its sequence, properties, and in its high specificity for SPP. This hydrophobic mammalian enzyme, which contains the Type 2 lipid phosphohydrolase conserved sequence motif, is $Mg^{2+}$-independent and shows high substrate specificity for SPP.

As described in the Examples below, when expressed in yeast, murine SPP can partially substitute for the function of LBP1. Membrane fractions from human embryonic kidney HEK293 cells transfected with mSPP1 markedly degraded SPP but not lysophosphatidic acid, phosphatidic acid, or ceramide-1-phosphate. Enforced expression of mSPP1 in NIH 3T3 fibroblasts markedly decreased survival and induced the characteristic traits of apoptosis. Collectively, the results presented herein indicate that mSPP1 regulates the dynamic balance between sphingosine and SPP levels in mammalian cells, and therefore can play an important role in regulating cell survival.

Polynucleotides

Polynucleotides useful in the present invention include those described herein and those that one of skill in the art will be able to derive therefrom following the teachings of this specification. A preferred aspect of the present invention is a recombinant polynucleotide encoding a murine mSPP1 protein. One preferred embodiment is a nucleic acid having the sequence disclosed in FIG. 1, SEQ ID NO:1 and disclosed as follows:

```
gccagtgcca agctaaaatt aaccctcact aaagggaata agcttgcggc cgctgcggcc    (SEQ ID NO:1)

tgttggcgcg gtcgccggca gcctcgagcg agtcgagcta ggcaccgtgg cggctgtggc tggcgaggag cgcgtggccg gatcaattcc cgagtggccc gcgaccatgt ccctggggca gcggctggct ctgctggcca gccgtctgca ggagccgcag cgggtggcga gcttccagcg tctgtgtggg gtggaggtgc cgctcagcag cccggcggcg gacgaggatg cagagaccga
```

-continued

```
ggttcgcgga gccccgggag aacccggcg acggggacgg cagccgggcg ctgaggacag ccccgccaag gcggactgct gcggtgcccc gaacggcgtg cgcaacgggc tggcggccga gccgggcccg accgggcccc gccgcgcggg ctcgcagcgc cgcaactcgt tgacgggcga ggagggcgag ctggtcaaag tgagcaactt gccgctctac tacctgttct gcctaggcac ggaactgggc aacgagctct tctacatctt attcttcccc ttctggatct ggaatctcga cccctttgtg ggccggaggc tggtgatcat ctgggtgctg gtcatgtacc tgggccagtg caccaaggac atcatccgct ggccacgcc ggcctcgccg cctgtcatca agctggaggt cttctacaac tcggaataca gcatgccctc cacgcatgcc atgtcaggca ccgccatccc catcgccatg ttcctgctca cctatggccg ctggcagtat cctcttatct acgggctgat tctcattccc tgctggagtt cactagtttg cctaagtaga atctacatgg gaatgcattc tatcctggat gtcattgctg gattcttgta taccatttta atcttaatta tcttctaccc attggtggac ctgattgaca acttcaacca aacttacaaa tatgcgccgc tcatcatcat cgggcttcac ttaattttgg gcatcttctc tttcacccctt gacacctgga gcacatcccg aggagacacg gctgagattc tgggaagtgg tgctgggatt gcatgtggct cacacgctgc ttataccctg ggcctatcct tagaaccttc tctgcacatg ttacccttag ctatcccccc tcttactgta actctgtttg gaaaagccat attacggatc gtcctaggaa tgctgcttgt actgttcgtg agggatatca tgaagaagat caccattcct ctagcctgta aactctccag tattccgtgt catgacattc gccaagcaag gcagcacatg gaagtggagc tgccataccg gtatattacc tacgggatgg ttgggttctc catcacgttt ttggtcccct atgtattttc ctttattggt atctcttgat ggaggaacac tgtttgttat aagaaaggag gctaccagct atatctaaag ctattctcta ggtaaaactt ggatcagagg cttctgcaag aatttgactt aaagaagtaa attctgcagc cagtgcattc tctcattgca caccagatgt tgttttacgt gggctgagct ctctcagtgc tgagaaatgg cgcgcccatt tagaatgttc accaaatgtt tggggagttc tgtgctgtta caaattgtag ttatatatac catatattaa ggcacacggt gtgcaaaggt gtgtctagta tatattatat atacaactgt ttacctaaca acagtggggt gtattgaaaa aaatcagtaa caatatgcag ttgtgcccag ttttttggaa ttaatgcagg catgttgagg cttctgcaag aatttgactt aaagaagtaa attctgcagc cagtgcattc tctcattgca caccagatgt tgttttacgt gggctgagct ctctcagtgc tgagaaatgg cgcgcccatt tagaatgttc accaaatgtt tggggagttc tgtgctgtta caaattgtag ttatatatac catatattaa ggcacacggt gtgcaaaggt gtgtctagta tatattatat atacaactgt ttacctaaca acagtggggt gtattgaaaa aaatcagtaa caatatgcag ttgtgcccag ttttttggaa ttaatgcagg catgttg
```

The translation initiation and termination codons are underlined. A particularly preferred embodiment is a polynucleotide comprising the coding sequence of mSPP1 of SEQ ID NO:1.

Another preferred aspect of the present invention is a recombinant polynucleotide encoding a murine mSPP1b protein. One preferred embodiment is a nucleic acid having the sequence disclosed in FIG. 2, SEQ ID NO:2 and disclosed as follows:

```
atgggagaag agctgggcca ctgtgtccaa atgagaaaaa gtaatgagag gggcaaacgt   (SEQ ID NO:2)

ttcagagagc agagagtaca gagagctcag ggaaaggtat cacaccacac caaagaagag
```

-continued

```
gaggagacaa gagtgagaca gatgagccaa ggctgggagg aaaaggagta tgggtactac ctgttctgct taggcacgga actgggcaac gagctcttct acatcttatt cttcccttc tggatctgga atctcgaccc ctttgtgggc cggaggctgg tgatcatctg ggtgctggtc atgtacctgg gccagtgcac caaggacatc atccgctggc cacggccggc ctcgccgcct gtcatcaagc tggaggtctt ctacaactcg gaatacagca tgccctccac gcatgccatg tcaggcaccg ccatccccat cgccatgttc ctgctcacct atggccgctg gcagtatcct cttatctacg ggctgattct cattccctgc tggagttcac tagtttgcct aagtagaatc tacatgggaa tgcattctat cctggatgtc attgctggat tcttgtatac cattttaatc ttaattatct tctacccatt ggtggacctg attgacaact tcaaccaaac ttacaaatat gcgccgctca tcatcatcgg gcttcactta attttgggca tcttctcttt caccttgac acctggagca catcccgagg agacacggct gagattctgg gaagtggtgc tgggattgca tgtggctcac acgctgctta taccctgggc ctatccttag aaccttctct gcacatgtta cccttagcta tcccccctct tactgtaact ctgtttggaa aagccatatt acggatcgtc ctaggaatgc tgcttgtact gttcgtgagg gatatcatga agaagatcac cattcctcta gcctgtaaac tctccagtat tccgtgtcat gacattcgcc aagcaaggca gcacatggaa gtggagctgc cataccggta tattacctac gggatggttg ggttctccat cacgttttttg gtcccctatg tattttcctt tattggtatc tcttga
```

The sequence of mSPP1b provided in SEQ ID NO:2 is the sequence that codes for the mSPP1b polypeptide. As described herein, mSPP1b polypeptide does not exhibit the enzymatic activity of the mSPP1 polypeptide and therefore is useful as a counterscreening agent or control. Therefore, for convenience in describing the various aspects of the invention relating to polypeptides, polynucleotides, recombinant constructs, cells lines, and methods of expressions etc., will be described with reference to mSPP1. However, the skilled artisan will recognize that the mSPP1b polynucleotides, polypeptides, host cells etc., can be likewise created as described for mSPP1.

The isolated nucleic acid molecules of the present invention can include a ribonucleic or deoxyribonucleic acid molecule, which can be single (coding or noncoding strand) or double stranded, as well as synthetic nucleic acid, such as a synthesized, single stranded polynucleotide.

The present invention also relates to recombinant vectors and recombinant hosts, both prokaryotic and eukaryotic, which contain the substantially purified nucleic acid molecules disclosed throughout this specification.

As used herein a "polynucleotide" is a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region(s) and/or other polynucleotide units commonly used in the art.

An "expression vector" is a polynucleotide having regulatory regions operably linked to a coding region such that, when in a host cell, the regulatory regions can direct the expression of the coding sequence. The use of expression vectors is well known in the art. Expression vectors can be used in a variety of host cells and, therefore, the regulatory regions are preferably chosen as appropriate for the particular host cell.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

Polynucleotides of this invention contain full length or partial length sequences of the mSPP1 gene sequences disclosed herein. Polynucleotides of this invention can be single or double stranded. If single stranded, the polynucleotides can be a coding, "sense," strand or a complementary, "antisense," strand. Antisense strands can be useful as modulators of the gene by interacting with RNA encoding the mSPP1 protein. Antisense strands are preferably less than full length strands having sequences unique or specific for RNA encoding the protein.

The polynucleotides can include deoxyribonucleotides, ribonucleotides or mixtures of both. The polynucleotides can be produced by cells, in cell-free biochemical reactions or through chemical synthesis. Non-natural or modified nucleotides, including inosine, methyl-cytosine, deazaguanosine, etc., can be present. Natural phosphodiester internucleotide linkages can be appropriate. However, polynucleotides can have non-natural linkages between the nucleotides. Non-natural linkages are well known in the art and include, without limitation, methylphosphonates, phosphorothioates, phosphorodithionates, phosphoroamidites and phosphate ester linkages. Dephospho-linkages are also known, as bridges between nucleotides. Examples of these include siloxane, carbonate, carboxymethyl ester, acetamidate, carbamate, and thioether bridges. "Plastic DNA," having, for example, N-vinyl, methacryloxyethyl, methacrylamide or ethyleneimine internucleotide linkages, can be used. "Peptide Nucleic Acid" (PNA) is also useful and resists degradation by nucleases. These linkages can be mixed in a polynucleotide.

As used herein, "purified" and "isolated" are utilized interchangeably to stand for the proposition that the polynucleotide, protein and polypeptide, or respective fragments thereof in question have been removed from the in vivo environment so that they exist in a form or purity not found in nature. Purified or isolated nucleic acid molecules can be manipulated by the skilled artisan, such as but not limited to sequencing, restriction digestion, site-directed mutagenesis, and subcloning into expression vectors for a nucleic acid fragment as well as obtaining the wholly or partially purified protein or protein fragment so as to afford the opportunity to generate polyclonal antibodies, monoclonal antibodies, or perform amino acid sequencing or peptide digestion. Therefore, the nucleic acids claimed herein can be present in whole cells or in cell lysates or in a partially or substantially purified form. It is preferred that the molecule be present at a concentration at least about five-fold to ten-fold higher than that found in nature. A polynucleotide is considered substantially pure if it is obtained purified from cellular components by standard methods at a concentration of at least about 100-fold higher than that found in nature. A polynucleotide is considered essentially pure if it is obtained at a concentration of at least about 1000-fold higher than that found in nature. We most prefer polynucleotides that have been purified to homogeneity, that is, at least 10,000–100,000 fold. A chemically synthesized nucleic acid sequence is considered to be substantially purified when purified from its chemical precursors by the standards stated above.

The term "recombinant" is used to denote those polynucleotide preparations, constructs, esxpressions systems and cell lines containing the same which are made by the hand of man.

Included in the present invention are assays that employ further novel polynucleotides that hybridize to mSPP1 sequences under stringent conditions. By way of example, and not limitation, a procedure using conditions of high stringency is as follows: Prehybridization of filters containing DNA is carried out for 2 hr. to overnight at 65° C. in buffer composed of 6×SSC, 5×Denhardt's solution, and 100 μg/ml denatured salmon sperm DNA. Filters are hybridized for 12 to 48 hrs at 65° C. in prehybridization mixture containing 100 μg/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography.

Other procedures using conditions of high stringency would include either a hybridization step carried out in 5×SSC, 5×Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook, et al., 1989, Molecular Cloning: A Laboratory Manual, second edition, Cold Spring Harbor Laboratory Press. In addition to the foregoing, other conditions of high stringency which may be used are well known in the art.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.,: (COMPUTATIONAL MOLECULAR BIOLOGY, Lesk, A. M., ed. Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds. Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCG program package (Devereux, J. et a., *Nucleic Acids Research* (1984) 12(1):387), BLAST?, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO:1, it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% identity to a reference amino acid sequence of SEQ ID NO:3 is intended that the amino acid sequence of the polypeptide is identical to the reference sequence except that the polypeptide sequence may include up to five amino acid alterations per each 100 amino acids of the reference amino acid of SEQ ID NO:3. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence of anywhere between those terminal positions, interspersed either individually among residues in the reference sequence or in one or more contiguous groups within the reference sequence.

Polypeptides

A preferred aspect of the present invention is a substantially purified form of the murine mSPP1 protein. A preferred embodiment is a protein that has the amino acid sequence which is shown in FIG. 3, in SEQ ID NO:3 and disclosed in single letter code as follows:

mSPP1 protein. For example, one can express N-terminal or C-terminal truncations, or internal additions or deletions, in host cells and test for their ability to catalyze the dephosphorylation of sphingosine-1-phosphate.

It is known that there is a substantial amount of redundancy in the various codons which code for specific amino

MSLGQRLALLASRLQEPQRVASFQRLCGVEVPLSSPAADEDAETEVRGAPGEPRRRGRQP  (SEQ ID NO:3)

GAEDSPAKADCCGAPNGVRNGLAAEPGPTGPRRAGSQRRNSLTGEEGELVKVSNLPLYYL

FCLGTELGNELFYILFFPFWIWNLDPFVGRRLVIIWVLVMYLGQCTKDIIRWPRPASPPV

IKLEVFYNSEYSMPSTHAMSGTAIPIAMFLLTYGRWQYPLIYGLILIPCWSSLVCLSRIY

MGMHSILDVIAGFLYTILILIIFYPLVDLIDNFNQTYKYAPLIIIGLHLILGIFSFTLDT

WSTSRGDTAEILGSGAGIACGSHAAYTLGLSLEPSLHMLPLAIPPLTVTLFGKAILRIVL

GMLLVLFVRDIMKKITIPLACKLSSIPCHDIRQARQHMEVELPYRYITYGMVGFSITFLV

PYVFSFIGIS

Another preferred aspect of the present invention is a substantially purified form of the murine mSPP1b protein. A preferred embodiment is a protein that has the amino acid sequence which is shown in FIG. 4, in SEQ ID NO:4 and disclosed in single letter code as follows:

acids. Therefore, this invention is also directed to those DNA sequences that encode RNA comprising alternative codons which code for the eventual translation of the identical amino acid.

MGEELGHCVQMRKSNERGKRFREQRVQRAQGKVSHHTKEEEETRVRQMSQGWEEKEYGYY  (SEQ ID NO:4)

LFCLGTELGNELFYILFFPFWIWNLDPFVGRRLVIIWVLVMYLGQCTKDIIRWPRPASPP

VIKLEVFYNSEYSMPSTHAMSGTAIPIAMFLLTYGRWQYPLIYGLILIPCWSSLVCLSRI

YMGMHSILDVIAGFLYTILILIIFYPLVDLIDNFNQTYKYAPLIIIGLHLILGIFSFTLD

TWSTSRGDTAEILGSGAGIACGSHAAYTLGLSLEPSLHMLPLAIPPLTVTLFGKAILRIV

LGMLLVLFVRDIMKKITIPLACKLSSIPCHDIRQARQHMEVELPYRYITYGMVGFSITFL

VPYVFSFIGIS

The mSPP1b polypeptide is described herein to lack the activity of the mSPP1 polypeptide. For convenience and clarity in the description of the invention, the invention will be described for the mSPP1 polypeptide. However, a skilled artisan will recognize that while the description refers to the active mSPP1 polypeptide and fragments thereof, one can create the corresponding polypeptides and fragments thereof from the mSPPb sequence.

The present invention also relates to biologically active fragments and mutant or polymorphic forms of the mSPP1 polypeptide sequence set forth as SEQ ID NO:3, including but not limited to amino acid substitutions, deletions, additions, amino terminal truncations and carboxy-terminal truncations such that these mutations provide for proteins or protein fragments of diagnostic, therapeutic or prophylactic use and would be useful for screening for modulators, and/or inhibitors of mSPP1 function.

Using the disclosure of polynucleotide and polypeptide sequences provided herein to isolate polynucleotides encoding naturally occurring forms of mSPP1, one of skill in the art can determine whether such naturally occurring forms are mutant or polymorphic forms of mSPP1 by sequence comparison. One can further determine whether the encoded protein, or fragments of any mSPP1 protein, are biologically active by routine testing of the protein of fragment in a in vitro or in vivo assay for the biological activity of the Therefore, the present invention discloses codon redundancy which can result in different DNA molecules encoding an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. However, any given change can be examined for any effect on biological function by simply assaying for the ability to catalyze the catabolism of sphingosine-1-phosphate as compared to an unaltered mSPP1 protein. The mSPP1b protein can be used as a negative control in these assessments.

It is known that DNA sequences coding for a peptide can be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate.

As used herein, a "biologically active equivalent" or "functional derivative" of a wild-type mSPP1 possesses a biological activity that is substantially similar to the biological activity of a wild type mSPP1. The term "functional derivative" is intended to include the "fragments," "mutants," "variants," "degenerate variants," "analogs," "orthologues," and "homologues" and "chemical derivatives" of a wild type mSPP1 protein that can catalyze the catabolism of sphingosine-1-phosphate.

The term "fragment" refers to any polypeptide subset of wild-type mSPP1. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the mSPP1. The term "variant" refers to a molecule substantially similar in structure and function to either the entire wild-type protein or to a fragment thereof. A molecule is "substantially similar" to a wild-type mSPP1-like protein if both molecules have substantially similar structures or if both molecules possess similar biological activity. Therefore, if the two molecules possess substantially similar activity, they are considered to be variants even if the exact structure of one of the molecules is not found in the other or even if the two amino acid sequences are not identical. The term "analog" refers to a molecule substantially similar in function to either the full-length mSPP1 protein or to a biologically active fragment thereof.

As used herein in reference to a mSPP1 gene or encoded protein, a "polymorphic" mSPP1 is a mSPP1 that is naturally found in the population of animals at large. Typically, the genes for polymorphs of mSPP1 can be detected by high stringency hybridization using the mSPP1 gene as a probe. A polymorphic form of mSPP1 can be encoded by a nucleotide sequence different from the particular mSPP1 gene disclosed herein as SEQ ID NO:1. However, because of silent mutations, a polymorphic mSPP1 gene can encode the same or different amino acid sequence as that disclosed herein. Further, some polymorphic forms mSPP1 will exhibit biological characteristics that distinguish the form from wild-type mSPP1 activity, in which case the polymorphic form is also a mutant.

A protein or fragment thereof is considered purified or isolated when it is obtained at least partially free from it's natural environment in a composition or purity not found in nature. It is preferred that the molecule be present at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature. It is most prefer proteins that have been purified to homogeneity, that is, at least 10,000–100,000 fold.

The term "recombinant" with respect to a polypeptide of the present invention refers only to polypeptides that are made by recombinant processes, expressed by recombinant cells or purified from natural cells as described above. Preparations having partially purified mSPP1 polypeptide are meant to be within the scope of the term "recombinant."

Expression of mSPP1

A variety of expression vectors can be used to express recombinant mSPP1 polypeptide in host cells. Expression vectors are defined herein as nucleic acid sequences that include regulatory sequences for the transcription of cloned DNA and the translation of their mRNAs in an appropriate host. Such vectors can be used to express a genes in a variety of hosts such as yeast, bacteria, bluegreen algae, plant cells, insect cells and animal cells. Specifically designed vectors allow the shuttling of genes between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and regulatory sequences. A promoter is defined as a regulatory sequence that directs RNA polymerase to bind to DNA and initiate RNA synthesis. A strong promoter is one which causes mRNAs to be initiated at high frequency. Expression vectors can include, but are not limited to, cloning vectors, modified cloning vectors, specifically designed plasmids or viruses.

In particular, a variety of bacterial expression vectors can be used to express recombinant mSPP1 in bacterial cells. Commercially available bacterial expression vectors which are suitable for recombinant mSPP1 expression include, but are not limited to pQE (QIAGEN), pET11a or pET15b (NOVAGEN), lambda gt11 (INVITROGEN), and pKK223-3 (PHARMACIA).

Alternatively, one can express mSPP1 DNA in cell-free transcription-translation systems, or mSPP1 RNA in cell-free translation systems. Cell-free synthesis of mSPP1 polypeptide can be in batch or continuous formats known in the art.

One can also synthesize mSPP1 chemically, although this method is not preferred.

A variety of host cells can be employed with expression vectors to synthesize mSPP1 protein. These can include *E. coli*, Bacillus, and Salmonella. Insect and yeast cells can also be appropriate. However, the most preferred host cell is a mammalian host cell.

Following expression of mSPP1 in a host cell, mSPP1 polypeptides can be recovered. Several protein purification procedures are available and suitable for use. mSPP1 protein and polypeptides can be purified from cell lysates and extracts, or from culture medium, by various combinations of, or individual application of methods including detergent solubilization, ultrafiltration, acid extraction, alcohol precipitation, salt fractionation, ionic exchange chromatography, phosphocellulose chromatography, lecithin chromatography, affinity (e.g., antibody or His-Ni) chromatography, size exclusion chromatography, hydroxylapatite adsorption chromatography and chromatography based on hydrophobic or hydrophillic interactions. In some instances, protein denaturation and refolding steps can be employed. High performance liquid chromatography (HPLC) and reversed phase HPLC can also be useful. Dialysis can be used to adjust the final buffer composition.

The mSPP1 protein itself is useful in assays to identify compounds that alter the activity of the protein—including compounds that inhibit or stimulate the activity of the protein. The mSPP1 protein is also useful for the generation of antibodies against the protein, structural studies of the protein, and structure/function relationships of the protein.

The mSPP1b protein, while being closely related to the mSPP1 protein, does not exhibit the activity of the mSPP1 protein. Therefore, the mSPP1b protein is useful in a counterscreen to asses the specificity of the interaction of a compound and a mSPP1 protein.

Modulators, Agonist, Antagonists and Inhibitors of mSPP1

The present invention is also directed to methods for screening for compounds which modulate the expression of, stimulate or inhibit the activity of a mSPP1 protein. Compounds which modulate or inhibit mSPP1 can be DNA, RNA, peptides, proteins, or non-proteinaceous organic or inorganic compounds or other types of molecules. Compounds that modulate the expression of DNA or RNA encoding mSPP1 or are agonists, antagonists or inhibitors of the biological function of mSPP1 can be detected by a variety of assays. The assay can be a simple "yes/no" assay to determine whether there is a change in expression or activity. The assay can be made quantitative by comparing the expression or activity of a test sample with the level or degree of expression or activity in a standard sample, that is, a control. A compound that is a modulator can be detected by measuring the amount of the mRNA and/or mSPP1 produced in the presence of the compound. A compound that is an agonist, antagonist or inhibitor can be detected by measuring the specific activity of the mSPP1 protein in the presence and absence of the compound.

The proteins, DNA molecules, RNA molecules and antibodies lend themselves to the formulation of kits suitable for the detection and anaysis of mSPP1. Such a kit would comprise a compartmentalized carrier suitable to hold in close confinement at least one container. The carrier would further comprise reagents such as recombinant mSPP1 or anti-mSPP1 antibodies suitable for detecting mSPP1. The carrier can also contain a means for detection such as labeled antigen or enzyme substrates or the like.

Assays

Assays of the present invention can be designed in many formats generally known in the art of screening compounds for biological activity or for binding to enzymes. Assays of the present invention can advantageously exploit the activity of mSPP1 in converting SPP to sphingosine or dihydrosphingosine-1-phosphate (DHSP) to dihydrosphingosine (DHS). For convenience, the description that follows will refer mostly to the conversion of SPP to sphingosine, however, either conversion can be followed in an assay.

The present invention includes methods of identifying compounds that specifically interact with mSPP1 polypeptides. Compounds that interact with the enzyme can stimulate or inhibit the activity of mSPP1. The specificity of binding of compounds having affinity for mSPP1 can be shown by measuring the affinity of the compounds to membranes from recombinant cells expressing a mSPP1 polypeptide. Expression of mSPP1 polypeptides and screening for compounds that bind to mSPP1 or that inhibit the conversion of SPP to sphingosine, provides an effective method for the rapid selection of compounds with affinity for mSPP1. The SPP can be radiolabeled but can also be labeled by other means known in the art and thereafter can be used to follow the conversion of the labelled SPP to sphingosine in assays of mSPP1 activity.

If one desires to produce a fragment of the mSPP1 or mutant, polymorphic or allelic variants of the mSPP1, one can test those products in the assays described below and compare the results to those obtained using an active mSPP1 polypeptide of SEQ ID NO:3 or inactive mSPP1b polypeptide of SEQ ID NO:4. In this manner one can easily assess the ability of the fragment, mutant, polymorph or allelic variant to bind compounds, be activated by agonists or be inactivated or inhibited by antagonists of mSPP1.

Therefore, the present invention includes assays by which compounds that are mSPP1 agonists, antagonists, and inhibitors may be identified. The assay methods of the present invention differ from those described in the art because the present assays incorporate at least one step wherein the interaction of SPP and an mSPP1 polypeptide is incorporated into the assay.

General methods for identifying ligands, agonists and antagonists are well known in the art and can be adapted to identify agonists and antagonists of mSPP1. The order of steps in any given method can be varied or performed concurrently as will be recognized by those of skill in the art of assays. The following is a sampling of the variety of formats that can be used to conduct an assay of the present invention.

Accordingly, the present invention includes a method for determining whether a candidate compound is an agonist or an inhibitor of mSPP1, the method of which comprises:

(a) transfecting cells with an expression vector encoding a mSPP1 polypeptide;

(b) allowing the transfected cells to grow for a time sufficient to allow mSPP1 to be expressed in the cells;

(c) exposing portions of the cells to labeled SPP in the presence and in the absence of the compound;

(d) measuring the conversion of the labeled SPP to sphingosine in the portions of cells; and (e) comparing the amount of conversion of SPP to DHS in the presence and the absence of the compound where a decrease in the amount of conversion of SPP to sphingosine in the presence of the compound indicates that the compound is an inhibitor of mSPP1 whereas an increase in the conversion of SPP to sphingosine indicates that the compound is an agonist of mSPP1.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. In this step the SPP and candidate compound can be applied to the cell sequentially or concurrently. It is preferred that the compound is applied first or that the compound and SPP are applied concurrently.

The above whole cell methods can be used in assays where one desires to assess whether a compound can traverse a cell membrane to interact with mSPP1. However, the above methods can be modified in that, rather than exposing the test cells to the candidate compound, membranes can be prepared from the cells and those membranes can be exposed to the compound. Such a modification utilizing membranes rather than cells is well known in the art and is described in, e.g., Hess et al., 1992. Particular methods of assaying membranes are described in the Examples below.

Accordingly, the present invention provides a method of using the interaction of SPP and mSPP1 for determining whether a candidate compound is an agonist or inhibitor of a mSPP1 polypeptide in membranes comprising:

(a) providing test cells by transfecting cells with an expression vector that directs the expression of mSPP1 in the cells;

(b) preparing membranes containing mSPP1 from the test cells;

(c) exposing the membranes to SPP under conditions such that the ligand binds to the polypeptide in the membranes;

(d) further exposing the membranes to a candidate compound under similar conditions;

(e) measuring the amount of conversion of SPP to sphingosine in the membranes in the presence and the absence of the compound;

(f) comparing the amount of conversion of SPP to sphingosine in the presence and the absence of the compound where a decrease in the amount of conversion of SPP to sphingosine in the presence of the compound indicates that the compound is an inhibitor of mSPP1; whereas an increase in the conversion of SPP to sphingosine indicates that the compound is an agonist of mSPP1.

As a further modification of the above-described methods, RNA encoding mSPP1 can be prepared as, e.g., by in vitro transcription using a plasmid containing mSPP1 under the control of a bacteriophage T7 promoter, and the RNA can be microinjected into Xenopus oocytes in order to cause the expression of mSPP1 in the oocytes. Compounds are then tested for binding to the mSPP1 or inhibition of activity of mSPP1 expressed in the oocytes. As in all assays of this invention, a step using the interaction of SPP and mSPP1 is incorporated into the assay.

Transgenic Animals

In reference to the transgenic animals of this invention, we refer to transgenes and genes. As used herein, a "transgene" is a genetic construct including a gene. The transgene is typically integrated into one or more chromosomes in the cells in an animal or its ancestor by methods known in the art. Once integrated, the transgene is carried in at least one place in the chromosomes of a transgenic animal. A gene is a nucleotide sequence that encodes a protein. The gene and/or transgene can also include genetic regulatory elements and/or structural elements known in the art.

The term "animal" is used herein to include all mammals, except humans. It also includes an individual animal in all stages of development, including embryonic and fetal stages. Preferably the animal is a rodent, and most preferably mouse or rat. A "transgenic animal" is an animal containing one or more cells bearing genetic information received, directly or indirectly, by deliberate genetic manipulation at a subcellular level, such as by microinjection or infection with recombinant virus. This introduced DNA molecule can be integrated within a chromosome, or it can be extra-chromosomally replicating DNA. Unless otherwise noted or understood from the context of the description of an animal, the term "transgenic animal" as used herein refers to a transgenic animal in which the genetic information was introduced into a germ line cell, thereby conferring the ability to transfer the information to offspring. If offspring in fact possess some or all of the genetic information, then they, too, are transgenic animals. The genetic information is typically provided in the form of a transgene carried by the transgenic animal.

The genetic information received by the non-human animal can be foreign to the species of animal to which the recipient belongs, or foreign only to the particular individual recipient. In the last case, the information can be altered or it can be expressed differently than the native gene. Alternatively, the altered or introduced gene can cause the native gene to become non-functional to produce a "knockout" animal.

As used herein, a "targeted gene" or "Knockout" (KO) transgene is a DNA sequence introduced into the germline of a non-human animal by way of human intervention, including but not limited to, the methods described herein. The targeted genes of the invention include nucleic acid sequences which are designed to specifically alter cognate endogenous alleles of the non-human animal.

An altered mSPP1 gene should not fully encode the same protein endogenous to the host animal, and its expression product can be altered to a minor or great degree, or absent altogether. In cases where it is useful to express a non-native mSPP1 protein in a transgenic animal in the absence of a endogenous mSPP1 protein we prefer that the altered mSPP1 gene induce a null, "knockout," phenotype in the animal. However a more modestly modified mSPP1 gene can also be useful and is within the scope of the present invention.

A type of target cell for transgene introduction is the embryonic stem cell (ES). ES cells can be obtained from pre-implantation embryos cultured in vivo and fused with embryos (M. J. Evans et al., Nature 292:154–156 (1981); Bradley et al., Nature 309:255–258 (1984); Gossler et al. Proc. Natl. Acad. Sci. USA 83:9065–9069 (1986); and Robertson et al., Nature 322:445–448 (1986)). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)). Animals are screened for those resulting in germline transformants. These are crossed to produce animals homozygous for the transgene.

Methods for evaluating the targeted recombination events as well as the resulting knockout mice are readily available and known in the art. Such methods include, but are not limited to DNA (Southern) hybridization to detect the targeted allele, polymerase chain reaction (PCR), polyacrylamide gel electrophoresis (PAGE) and Western blots to detect DNA, RNA and protein.

This may have a therapeutic aim. The presence of a mutant, allele or variant sequence within cells of an organism, particularly when in place of a homologous endogenous sequence, may allow the organism to be used as a model in testing and/or studying the role of the mSPP1 gene or substances which modulate activity of the encoded polypeptide and/or promoter in vivo or are otherwise indicated to be of therapeutic potential.

EXAMPLE 1

Identification of Mammalian Homologs to Yeast Sphingosine-1-Phosphate Phosphatases To identify the mammalian homolog of the yeast sphingosine-1-phosphate (SPP) phosphatase encoded by LBP1, the EST database was searched using the TBLASTN algorithm. Sequences that gave the best scores were further analyzed for the presence of the conserved amino acid residues identified as important for coordination and hydrolysis of the phosphate ester substrates of Type 2 lipid phosphate phosphohydrolases ($KX_6RP-X_{12-54}-PSGH-X_{31-54}-SRX_5HX_3D$). A mouse clone (gb:AA574626) was identified as having the expected conserved amino acids and better homology to the yeast SPP phosphatases than to the previously cloned mammalian Type 2 glycerolipid phosphatases known as LPP1/PAP2a, LPP2/PAP2c, and LPP3/PAP2b.

A bacterial culture transformed with this EST clone was ordered from ATCC (1247076) and plasmid DNA was prepared using WIZARD DNA Purification System (PROMEGA). DNA preparations were subjected to automated sequence analysis using the PRISM Dye Deoxy terminator cycle sequencing kit (APPLIED BIOSYSTEMS, Foster City, Calif.) on an ABI PRISM 377 instrument. T7 and M13 sequencing primers that were complementary to the vector at sites flanking the EST clone were used in the sequencing reaction. Database searches (GENBANK, EMBL, SWISS-PROTEIN, PIR, dEST) sequence alignments, and analysis of the nucleotide and protein sequences were carried out using TBLAST and the GCG Sequence Analysis Software Package (Madison, Wis.).

Sequence alignments to LBP1 confirmed the homology throughout the phosphatase domains, but indicated that the clone was truncated, lacking sequence at the 5' and 3' ends. Alignments to mammalian proteins did not identify any known genes with significant homology, but several other EST clones had overlapping sequences. These clones were ordered and sequenced as above. In particular, a mouse clone (gb:AI098466, ATCC: 1664615) was identified as having additional 5' sequence, including the putative initiator MET codon and a Kozak consensus sequence.

EXAMPLE 2
RACE PCR Cloning mSPP1 and mSPP1b

To clone the 5' and 3' ends of the SPP phosphatase gene, a RACE (Rapid Amplification of cDNA Ends) methodology was employed in which gene specific PCR primers were designed based on EST AA574626 sequence data. The gene specific primers had a 50–70% GC content and Tm$\geq$70° C. The primers were paired with adapter primers and used to amplify the 5' and 3' ends using adapter ligated double stranded cDNAs and PCR kits purchased from CLONTECH (Marathon-Ready mouse brain cDNA, Marathon cDNA Amplification Kit, and Advantage PCR polymerase).

Primers used to clone the 5' end of the SPP phosphatase gene were
5'-GGCAAACTAGTGAACTCCAACAGGG (SEQ ID NO:5),
5'-CCAGGTACATGACCAGCACCCAG (SEQ ID NO:6) and
5'-CATGGCATGCGTGGAGGGCATGC (SEQ ID NO:7)
and primers used to clone the 3' end of the SPP phosphatase gene were
5'-CGGAACTGGGCAACGAGCTCTTC (SEQ ID NO:8) and
5'-CTCGGAATACAGCATGCCCTCCACGC (SEQ ID NO:9).

An APPLIED BIOSYSTEMS GENEAMP PCR 9700 instrument was used with cycling conditions of: 94° C. for 1 min; 5 cycles of 94° C. for 30 sec and 72° C. for 4 min; 5 cycles of 94° C. for 30 sec and 70° C. for 4 min; 30 cycles of 94° C. for 30 sec, 68° C. for 4 min; 70° C. for 7 min; and then hold at 4° C.

RACE products were subjected to additional PCR amplification rounds using nested primers to confirm that the products had been correctly primed with the gene specific sequences. PCR products were isolated on 1% TAE agarose gels, purified by GENECLEAN (BIO101) and ligated into pCR2.1 using a TA cloning kit (INVITROGEN). Ligation reactions were transformed into DH5alpha competent cells (BRL), plated onto LB agar containing Ampicillin and incubated overnight at 37° C. Individual colonies were inoculated into 4 ml LB media containing Ampicillin, incubated overnight at 37° C., and plasmid DNA was isolated using WIZARD DNA Purification System (PROMEGA).

The sequence of the 2.6 Kb 3' RACE PCR product from plasmid 3'RACE-pCR2.1 included sequence identical to EST AA574626 and additional 3' sequence containing the putative stop codon for the SPP phosphatase. The sequence of the 1.5 Kb 5' RACE product from plasmid 5'RACE-pCR2.1 diverged from the EST sequences except for a 224 bp overlap with the 5' end of EST AA574626.

EXAMPLE 3
Construction of mSPP1 and mSPP1b Clones for Expression

Two distinct clones were constructed with divergent 5' ends. The mSPP1 sequence contains the 5' end from EST AI098466, and the mSPP1b sequence contains the 5' end from the RACE PCR product. To construct mSPP1b, an internal BstYI restriction site found in the overlapping sequence of the 5' and 3' RACE products was used to join the two fragments. Plasmid 5'RACE-pCR2.1 was digested with ApaI and BstYI and a 0.3 Kb fragment was gel purified. Plasmid 3'RACE-pCR2.1 was digest with BstYI and PstI and a 1 Kb fragment was gel purified. The two fragments were ligated with ApaI and PstI cut mammalian expression vector pcDNA3.1zeo (INVITROGEN) to make plasmid mSPP1b-pcDNA3.1. To construct mSPP1, a 0.5 Kb HindIII/BstYI fragment from EST AI098466 and a 1 Kb BstYI/EcoRI from mSPP1b-pcDNA3.1 were ligated with HindIII/EcoRI cut pcDNA3.1, resulting in plasmid mSPP1-pcDNA3.1.

Ligation reactions were transformed into DH5alpha competent cells (BRL), plated onto LB agar containing Ampicillin and incubated overnight at 37° C. Individual colonies were inoculated into 4 ml LB media containing Ampicillin, incubated overnight at 37° C., and plasmid DNA was isolated using WIZARD DNA Purification System (PROMEGA). The nucleotide sequences of the intact mSPP1 and mSPP1b genes were determined.

EXAMPLE 4
Measurement of Phosphatase Activity in Yeast Extracts

To test whether mSPP1 and mSPP1b encoded SPP phosphatases with properties similar to yeast Lbp1p, the mouse genes were subcloned into pRS414-ADH for expression of the genes in LBP1 mutants under the control of a strong, constitutive yeast promoter (ADH). The resulting plasmids were mSPP1pRS414-ADH and mSPP1bpRS414-ADH. Yeast (lbp1$\Delta$::LEU2 sur2-2) were transformed with mSPP1pRS414-ADH, mSPP1bpRS414-ADH, or control vector (pRS414-ADH) using the lithium acetate/polyethylene glycol procedure and plated onto Synthetic Complete-Tryptophan (SC-TRP) Yeast Nitrogen Base medium (DIFCO) containing 1.5% agar, 2% glucose and 0.078% tryptophan-free supplement mixture (BIO101). Transformants were inoculated into SC-TRP media and incubated overnight at 30° C. to an OD600 of 1.0. Cells were collected by centrifugation and suspended in buffer containing 50 mM HEPES, pH 7.5, 5 mM DTT, 1 mM PMSF, and 1 $\mu$g/ml each chymostatin, aprotinin, and pepstatin. Cells were disrupted with glass beads (0.5 mm) in a Mini Bead Beater (BIOSPEC PRODUCTS, Bartlesville Okla.) and homogenates were cleared by centrifugations at 3,000×g for 10 min, and 9,500×g for 10 min.

Microsomal membranes were collected by ultracentrifugation (100,000×g, 1 hour) and suspended in disruption buffer containing 20% glycerol. Dihydrosphingosine-1-phosphate phosphohydrolase activity was measured in 200 $\mu$l containing 50 mM KPO$_4$ pH 7.2, 0.02% tergitol (NP-40), 2 $\mu$M [$^3$H]dihydrosphingosine-1-phosphate (40,000 cpm), 2 mM semicarbazide, and 0.3 to 5 $\mu$g of membrane protein. Following a 45 min incubation at 37° C., the assay was terminated with 200 $\mu$l 7 M NH$_4$OH. One ml of chloroform-:methanol (3:2) was added and 50 $\mu$l of the chloroform layer was counted by liquid scintillation.

Compared to the vector control, cells expressing mSPP1 had a 3 to 4 fold increase in membrane dihydrosphingosine-1-phosphate phosphohydrolase activity, but cells expressing mSPP1b had the same level of phosphohydrolase activity as control.

EXAMPLE 5
Expression of mSPP1 and mSPP1b in Yeast

Yeast cells defective in LBP1 shunt sphingolipid metabolites into phosphatidylethanolamine and phosphatidylcholine synthesis and become extremely sensitive to ceramide synthase inhibition by the antifungal agent, australifungin. To test whether the mouse SPP phosphatases can substitute for the function of LBP1, mSPP1pRS414-ADH, mSPP1bpRS414-ADH, or control vector (pRS414-ADH) were transformed into lbp1Δ::LEU2sur2-2 and sensitivity to australifungin was determined using a microtiter broth dilution assay. Transformants were incubated overnight in Synthetic Complete-Tryptophan (SC-TRP) Yeast Nitrogen Base medium (DIFCO) containing 2% glucose and 0.078% tryptophan-free supplement mixture (BIO101) at 33° C. Cells were inoculated at an $OD_{600}$=0.001 (~1×10$^4$ yeast cells/ml), and serial 2-fold dilutions of australifungin were made from 5 μg/ml. Growth after 48 h at 30° C. was measured by absorbance readings with a Rainbow spectrometer (TECAN).

Expression of mSPP1 partially reversed australifungin sensitivity of the lbp1Δsur2-2 mutant, giving a 64-fold increase in the $MIC_{90}$ compared to vector transformed mutants. In contrast, expression of mSPP1b did not alter australifungin sensitivity.

EXAMPLE 6
Expression of Phosphatase Activity in Mammalian Cells

Transfection-quality DNA was prepared for plasmids mSPP1-pcDNA3.1 and mSPP1b-pcDNA3.1 using endotoxin-free QIAGEN Maxi protocol (QIAGEN, Chatsworth, Calif.). Human embryonic kidney (HEK293) cells were maintained in high glucose Dulbecco's modified Eagle's medium (DMEM) containing 100 U/ml penicillin, 100 μg/ml streptomycin and 2 mM L-glutamine supplemented with 10% fetal bovine serum. Cells (1×10$^6$) were transfected with 20 μg of plasmid DNA by the $CaCl_2$ procedure using a kit from SPECIALTY MEDIA (Lavallette, N.J.). Cells were harvested 48 hours after transfection with enzyme-free dissociation solution (SPECIALTY MEDIA, Lavallette, N.J.). The cells were washed 3 times in cold PBS and then lysed in hypotonic buffer consisting of 1 mM TrisCl pH 7.2 and a protease inhibitor cocktail for 10 min at 4° C. Cell debris was removed by centrifugation at 1,000×g for 5 min at 4° C., and the supernatant fluid was recentrifuged at 40,000×g for 30 min. The pellet was suspended at a protein concentration of approximately 2 mg/ml in 40 mM Tris/Cl pH 7.5, protease inhibitor cocktail, and 20% glycerol. Dihydrosphingosine phosphate phosphohydrolase activity was measured as described in Example 4.

Expression of mSPP1 in HEK293 resulted in a 4 to 5 fold increase in dihydrosphingosine phosphate phosphohydrolase activity compared to vector transfected cells or mSPP1b transfected cells.

EXAMPLE 7
mRNA Expression of mSPP1 in Mammalian Tissues

Poly(A)+ RNA blots containing 2 μg of RNA from mouse adult tissues (CLONTECH) were probed with a 590 bp EagI/EcoRV fragment from mSPP1 that was gel purified and labeled with $^{32}$P-dCTP by random priming. Blots were hybridized in EXPRESSHYB Solution (CLONTECH) at 68° C. for 1 h and washed following the manufacturer's protocol. Bands were quantified using a MOLECULAR DYNAMICS STORM 860 and normalized to the amount of actin message present.

A single 3.8 kb transcript was detected in all tissues with highest levels in liver and kidney, and barely detectable levels in skeletal muscle. A corresponding 3.8 kb transcript was detected in over 30 human tissues that were surveyed indicating that this gene is ubiquitously expressed in humans.

EXAMPLE 8

Inhibitors and Activators of SPP Phosphatase Activity

Inhibitors and activators of mSPP1 can be identified in the $^3$H-dihydrosphingosine-1-phosphate phosphatase assay. Compounds diluted in DMSO, methanol, or other solvent, are added to assays with membranes prepared from cells expressing mSPP1, and dihydrosphingosine-1-phosphate phosphatase activity is measured as in Example 4. Compounds that reduce the $^3$H-dihydrosphingosine recovered in the chloroform layer are inhibitors of phosphatase activity, while compounds that increase $^3$H-dihydrosphingosine are activators. A semi-high throughput dihydrosphingosine-1-phosphate phosphohydrolase assay can be run in tube strips with an assay volume of 100 μl containing 50 mM $KPO^4$ pH 7.2, 0.02% tergitol (NP-40), 2 μM [$^3$H]dihydrosphingosine-1-phosphate (40,000 cpm), 2 mM semicarbazide, and membrane protein prepared from mSPP1 expressing cells. Following a 45 min incubation at 37° C., the assay can be terminated with 100 μl 7 M $NH_4OH$ and 0.5 ml of chloroform:methanol (3:2). Using a robotic pipetting station, 50 μl of the chloroform layer can be distributed into a 96-well T-tray (WALLAC). The T-trays can be air dried, scintillant added, and then counted in a Betaplate scintillation counter (WALLAC).

EXAMPLE 9

Yeast Based Screen for Inhibitors of SPP Phosphatase

Yeast sphingoid base phosphate phosphatase activity is not essential except in combination with other mutations in sphingolipid metabolism. One such lethal combination is lbp1Δdpl1Δsur2Δ, which will be dependent on functional expression of mSPP1 for growth and survival. To construct the strain that carries disruptions of the essential combination of 3 yeast genes and expresses mSPP1 for growth, mSPP1pRS414-ADH/TRP can be transformed into a diploid strain lbp1Δ::LEU2/LBP1, dpl1Δ::HIS3/dpl1Δ::HIS3, sur2Δ::URA3/sur2Δ::URA3, sporulated, and Trp+, Leu+, His+, Ura+ segregants can be isolated. Inhibitors of mSPP1 phosphatase activity should inhibit the growth of the strain, which can be measured in a 96-well or 384-well spectrophotometric assay.

Compounds diluted in DMSO, methanol, or other solvent, are added to wells and inoculated with logarithmic phase cells incubated in SC-TRP media. After 24 hours incubation at 30° C., the $OD_{600}$ can be measured in a microplate spectrophotometer. Compounds that reduce the $OD_{600}$ compared to solvent treated cells are potential inhibitors. To distinguish specific mSPP1 phosphatase inhibitors from compounds that inhibit yeast growth via other mechanisms, the compounds can be tested for growth inhibition against a wild-type strain, which does not require SPP phosphatase activity for growth, and the compounds can also be screened in an in vitro mSPP1 phosphatase assay as described above.

The Examples have been provided as guidance in practicing the invention and are not limiting of the scope of the invention which is defined by the following claims.

What is claimed:

1. A recombinant polynucleotide selected from the group consisting of:
   (a) a polynucleotide encoding a polypeptide having an amino acid sequence of SEQ ID NO:3,
   (b) a polynucleotide having the nucleotide sequence of SEQ ID NO:1, and
   (c) a polynucleotide which is fully complementary to the polynucleotide of (a) or (b).

2. The polynucleotide of claim 1 wherein the polynucleotide comprises nucleotides selected from the group consisting of natural, non-natural and modified nucleotides.

3. The polynucleotide of claim 1 wherein the internucleotide linkages are selected from the group consisting of natural and non-natural linkages.

4. An expression vector comprising a polynucleotide of claim 1.

5. An isolated host cell comprising the expression vector of claim 4.

6. A process for expressing a mSPP1 protein from a recombinant host cell, comprising:
   (a) transforming a suitable host cell with an expression vector of claim 4; and,
   (b) culturing the host cell of step (a) in conditions under which allow expression of said the mSPP1 protein from said expression vector.

* * * * *

SEQUENCE LISTING

<160> NUMBER OF SEQ ID NOS: 9

<210> SEQ ID NO 1
<211> LENGTH: 2197
<212> TYPE: DNA
<213> ORGANISM: Mouse

<400> SEQUENCE: 1

| | | | | | |
|---|---|---|---|---|---|
| gccagtgcca | agctaaaatt | aaccctcact | aaagggaata | agcttgcggc | cgctgcggcc | 60 |
| tgttggcgcg | gtcgccggca | gcctcgagcg | agtcgagcta | ggcaccgtgg | cggctgtggc | 120 |
| tggcgaggag | cgcgtggccg | gatcaattcc | cgagtggccc | cgaccatgt | ccctggggca | 180 |
| gcggctggct | ctgctggcca | gccgtctgca | ggagccgcag | cgggtggcga | gcttccagcg | 240 |
| tctgtgtggg | gtggaggtgc | cgctcagcag | cccggcggcg | gacgaggatg | cagagaccga | 300 |
| ggttcgcgga | gccccgggag | aaccccggcg | acggggacgg | cagccgggcg | ctgaggacag | 360 |
| ccccgccaag | gcggactgct | gcggtgcccc | gaacggcgtg | cgcaacgggc | tggcggccga | 420 |
| gccgggcccg | accgggcccc | gccgcgcggg | ctcgcagcgc | cgcaactcgt | tgacgggcga | 480 |
| ggagggcgag | ctggtcaaag | tgagcaactt | gccgctctac | tacctgttct | gcctaggcac | 540 |
| ggaactgggc | aacgagctct | tctacatctt | attcttcccc | ttctggatct | ggaatctcga | 600 |
| cccctttgtg | ggccggaggc | tggtgatcat | ctgggtgctg | gtcatgtacc | tgggccagtg | 660 |
| caccaaggac | atcatccgct | ggccacggcc | ggcctcgccg | cctgtcatca | agctggaggt | 720 |
| cttctacaac | tcggaataca | gcatgccctc | cacgcatgcc | atgtcaggca | ccgccatccc | 780 |
| catcgccatg | ttcctgctca | cctatggccg | ctggcagtat | cctcttatct | acgggctgat | 840 |
| tctcattccc | tgctggagtt | cactagtttg | cctaagtaga | atctacatgg | gaatgcattc | 900 |
| tatcctggat | gtcattgctg | gattcttgta | taccatttta | atcttaatta | tcttctaccc | 960 |
| attggtggac | ctgattgaca | acttcaacca | aacttacaaa | tatgcgccgc | tcatcatcat | 1020 |
| cgggcttcac | ttaattttgg | gcatcttctc | tttcacccct | gacacctgga | gcacatcccg | 1080 |
| aggagacacg | gctgagattc | tgggaagtgg | tgctgggatt | gcatgtggct | cacacgctgc | 1140 |
| ttataccctg | ggcctatcct | tagaaccttc | tctgcacatg | ttacccttag | ctatcccccc | 1200 |
| tcttactgta | actctgtttg | gaaaagccat | attacggatc | gtcctaggaa | tgctgcttgt | 1260 |
| actgttcgtg | agggatatca | tgaagaagat | caccattcct | ctagcctgta | aactctccag | 1320 |
| tattccgtgt | catgacattc | gccaagcaag | gcagcacatg | gaagtggagc | tgccataccg | 1380 |
| gtatattacc | tacgggatgg | ttgggttctc | catcacgttt | ttggtcccct | atgtattttc | 1440 |
| ctttattggt | atctcttgat | ggaggaacac | tgtttgttat | aagaaaggag | gctaccagct | 1500 |
| atatctaaag | ctattctcta | ggtaaaactt | ggatcagagg | cttctgcaag | aatttgactt | 1560 |
| aaagaagtaa | attctgcagc | cagtgcattc | tctcattgca | caccagatgt | tgttttacgt | 1620 |
| gggctgagct | ctctcagtgc | tgagaaatgg | cgcgcccatt | tagaatgttc | accaaatgtt | 1680 |
| tggggagttc | tgtgctgtta | caaattgtag | ttatatatac | catatattaa | ggcacacggt | 1740 |
| gtgcaaaggt | gtgtctagta | tatattatat | atacaactgt | ttacctaaca | acagtggggt | 1800 |
| gtattgaaaa | aaatcagtaa | caatatgcag | ttgtgcccag | gtttttggaa | ttaatgcagg | 1860 |
| catgttgagg | cttctgcaag | aatttgactt | aaagaagtaa | attctgcagc | cagtgcattc | 1920 |
| tctcattgca | caccagatgt | tgttttacgt | gggctgagct | ctctcagtgc | tgagaaatgg | 1980 |
| cgcgcccatt | tagaatgttc | accaaatgtt | tggggagttc | tgtgctgtta | caaattgtag | 2040 |

```
ttatatatac catatattaa ggcacacggt gtgcaaaggt gtgtctagta tatattatat      2100
atacaactgt ttacctaaca acagtggggt gtattgaaaa aaatcagtaa caatatgcag      2160
ttgtgcccag gtttttggaa ttaatgcagg catgttg                               2197

<210> SEQ ID NO 2
<211> LENGTH: 1116
<212> TYPE: DNA
<213> ORGANISM: Mouse

<400> SEQUENCE: 2
atgggagaag agctgggcca ctgtgtccaa atgagaaaaa gtaatgagag gggcaaacgt        60
ttcagagagc agagagtaca gagagctcag ggaaaggtat cacaccacac caaagaagag       120
gaggagacaa gagtgagaca gatgagccaa ggctgggagg aaaaggagta tgggtactac       180
ctgttctgct taggcacgga actgggcaac gagctcttct acatcttatt cttccccttc       240
tggatctgga atctcgaccc ctttgtgggc cggaggctgg tgatcatctg ggtgctggtc       300
atgtacctgg gccagtgcac caaggacatc atccgctggc cacggccggc ctcgccgcct       360
gtcatcaagc tggaggtctt ctacaactcg aatacagca tgccctccac gcatgccatg        420
tcaggcaccg ccatccccat cgccatgttc ctgctcacct atggccgctg gcagtatcct       480
cttatctacg ggctgattct cattccctgc tggagttcac tagtttgcct aagtagaatc       540
tacatgggaa tgcattctat cctggatgtc attgctggat tcttgtatac catttaatc        600 ttaattatct tctacccatt ggtggacctg attgacaact caaccaaac ttacaaatat         660 gcgccgctca tcatcatcgg gcttcactta attttgggca tcttctcttt caccttgac         720 acctggagca catcccgagg agacacggct gagattctgg gaagtggtgc tgggattgca       780
tgtggctcac acgctgctta taccctgggc ctatccttag aaccttctct gcacatgtta       840
cccttagcta tcccccctct tactgtaact ctgtttggaa aagccatatt acggatcgtc       900
ctaggaatgc tgcttgtact gttcgtgagg gatatcatga agaagatcac cattcctcta       960
gcctgtaaac tctccagtat tccgtgtcat gacattcgcc aagcaaggca gcacatggaa      1020
gtggagctgc ataccggta tattacctac gggatggttg ggttctccat cacgtttttg       1080
gtcccctatg tattttcctt tattggtatc tcttga                                1116

<210> SEQ ID NO 3
<211> LENGTH: 430
<212> TYPE: PRT
<213> ORGANISM: Mouse

<400> SEQUENCE: 3

Met Ser Leu Gly Gln Arg Leu Ala Leu Leu Ala Ser Arg Leu Gln Glu
  1               5                  10                  15

Pro Gln Arg Val Ala Ser Phe Gln Arg Leu Cys Gly Val Glu Val Pro
                 20                  25                  30

Leu Ser Ser Pro Ala Ala Asp Glu Asp Ala Glu Thr Glu Val Arg Gly
             35                  40                  45

Ala Pro Gly Glu Pro Arg Arg Gly Arg Gln Pro Gly Ala Glu Asp
         50                  55                  60

Ser Pro Ala Lys Ala Asp Cys Cys Gly Ala Pro Asn Gly Val Arg Asn
 65                  70                  75                  80

Gly Leu Ala Ala Glu Pro Gly Thr Gly Pro Arg Arg Ala Gly Ser
                 85                  90                  95
```

```
Gln Arg Arg Asn Ser Leu Thr Gly Glu Glu Gly Glu Leu Val Lys Val
                100                 105                 110

Ser Asn Leu Pro Leu Tyr Tyr Leu Phe Cys Leu Gly Thr Glu Leu Gly
            115                 120                 125

Asn Glu Leu Phe Tyr Ile Leu Phe Phe Pro Phe Trp Ile Trp Asn Leu
        130                 135                 140

Asp Pro Phe Val Gly Arg Arg Leu Val Ile Ile Trp Val Leu Val Met
145                 150                 155                 160

Tyr Leu Gly Gln Cys Thr Lys Asp Ile Ile Arg Trp Arg Pro Ala
                165                 170                 175

Ser Pro Pro Val Ile Lys Leu Glu Val Phe Tyr Asn Ser Glu Tyr Ser
            180                 185                 190

Met Pro Ser Thr His Ala Met Ser Gly Thr Ala Ile Pro Ile Ala Met
        195                 200                 205

Phe Leu Leu Thr Tyr Gly Arg Trp Gln Tyr Pro Leu Ile Tyr Gly Leu
            210                 215                 220

Ile Leu Ile Pro Cys Trp Ser Ser Leu Val Cys Leu Ser Arg Ile Tyr
225                 230                 235                 240

Met Gly Met His Ser Ile Leu Asp Val Ile Ala Gly Phe Leu Tyr Thr
                245                 250                 255

Ile Leu Ile Leu Ile Ile Phe Tyr Pro Leu Val Asp Leu Ile Asp Asn
            260                 265                 270

Phe Asn Gln Thr Tyr Lys Tyr Ala Pro Leu Ile Ile Gly Leu His
            275                 280                 285

Leu Ile Leu Gly Ile Phe Ser Phe Thr Leu Asp Thr Trp Ser Thr Ser
        290                 295                 300

Arg Gly Asp Thr Ala Glu Ile Leu Gly Ser Gly Ala Gly Ile Ala Cys
305                 310                 315                 320

Gly Ser His Ala Ala Tyr Thr Leu Gly Leu Ser Leu Glu Pro Ser Leu
                325                 330                 335

His Met Leu Pro Leu Ala Ile Pro Pro Leu Thr Val Thr Leu Phe Gly
            340                 345                 350

Lys Ala Ile Leu Arg Ile Val Leu Gly Met Leu Leu Val Leu Phe Val
        355                 360                 365

Arg Asp Ile Met Lys Lys Ile Thr Ile Pro Leu Ala Cys Lys Leu Ser
370                 375                 380

Ser Ile Pro Cys His Asp Ile Arg Gln Ala Arg Gln His Met Glu Val
385                 390                 395                 400

Glu Leu Pro Tyr Arg Tyr Ile Thr Tyr Gly Met Val Gly Phe Ser Ile
            405                 410                 415

Thr Phe Leu Val Pro Tyr Val Phe Ser Phe Ile Gly Ile Ser
            420                 425                 430

<210> SEQ ID NO 4
<211> LENGTH: 371
<212> TYPE: PRT
<213> ORGANISM: Mouse

<400> SEQUENCE: 4

Met Gly Glu Glu Leu Gly His Cys Val Gln Met Arg Lys Ser Asn Glu
1               5                   10                  15

Arg Gly Lys Arg Phe Arg Glu Gln Arg Val Gln Arg Ala Gln Gly Lys
                20                  25                  30

Val Ser His His Thr Lys Glu Glu Glu Thr Arg Val Arg Gln Met
            35                  40                  45
```

```
Ser Gln Gly Trp Glu Lys Glu Tyr Gly Tyr Leu Phe Cys Leu
    50                  55                  60

Gly Thr Glu Leu Gly Asn Glu Leu Phe Tyr Ile Leu Phe Pro Phe
65                  70                  75                  80

Trp Ile Trp Asn Leu Asp Pro Phe Val Gly Arg Arg Leu Val Ile Ile
                85                  90                  95

Trp Val Leu Val Met Tyr Leu Gly Gln Cys Thr Lys Asp Ile Ile Arg
                100                 105                 110

Trp Pro Arg Pro Ala Ser Pro Pro Val Ile Lys Leu Glu Val Phe Tyr
            115                 120                 125

Asn Ser Glu Tyr Ser Met Pro Ser Thr His Ala Met Ser Gly Thr Ala
    130                 135                 140

Ile Pro Ile Ala Met Phe Leu Leu Thr Tyr Gly Arg Trp Gln Tyr Pro
145                 150                 155                 160

Leu Ile Tyr Gly Leu Ile Leu Ile Pro Cys Trp Ser Ser Leu Val Cys
                165                 170                 175

Leu Ser Arg Ile Tyr Met Gly Met His Ser Ile Leu Asp Val Ile Ala
                180                 185                 190

Gly Phe Leu Tyr Thr Ile Leu Ile Leu Ile Ile Phe Tyr Pro Leu Val
                195                 200                 205

Asp Leu Ile Asp Asn Phe Asn Gln Thr Tyr Lys Tyr Ala Pro Leu Ile
    210                 215                 220

Ile Ile Gly Leu His Leu Ile Leu Gly Ile Phe Ser Phe Thr Leu Asp
225                 230                 235                 240

Thr Trp Ser Thr Ser Arg Gly Asp Thr Ala Glu Ile Leu Gly Ser Gly
                245                 250                 255

Ala Gly Ile Ala Cys Gly Ser His Ala Ala Tyr Thr Leu Gly Leu Ser
                260                 265                 270

Leu Glu Pro Ser Leu His Met Leu Pro Leu Ala Ile Pro Leu Thr
    275                 280                 285

Val Thr Leu Phe Gly Lys Ala Ile Leu Arg Ile Val Leu Gly Met Leu
    290                 295                 300

Leu Val Leu Phe Val Arg Asp Ile Met Lys Lys Ile Thr Ile Pro Leu
305                 310                 315                 320

Ala Cys Lys Leu Ser Ser Ile Pro Cys His Asp Ile Arg Gln Ala Arg
                325                 330                 335

Gln His Met Glu Val Glu Leu Pro Tyr Arg Tyr Ile Thr Tyr Gly Met
                340                 345                 350

Val Gly Phe Ser Ile Thr Phe Leu Val Pro Tyr Val Phe Ser Phe Ile
                355                 360                 365

Gly Ile Ser
    370

<210> SEQ ID NO 5
<211> LENGTH: 25
<212> TYPE: DNA
<213> ORGANISM: Mouse

<400> SEQUENCE: 5
ggcaaactag tgaactccaa caggg                                   25

<210> SEQ ID NO 6
<211> LENGTH: 23
<212> TYPE: DNA
<213> ORGANISM: Mouse
```

```
<400> SEQUENCE: 6
ccaggtacat gaccagcacc cag                                          23

<210> SEQ ID NO 7
<211> LENGTH: 23
<212> TYPE: DNA
<213> ORGANISM: Mouse

<400> SEQUENCE: 7
catggcatgc gtggagggca tgc                                          23

<210> SEQ ID NO 8
<211> LENGTH: 23
<212> TYPE: DNA
<213> ORGANISM: Mouse

<400> SEQUENCE: 8
cggaactggg caacgagctc ttc                                          23

<210> SEQ ID NO 9
<211> LENGTH: 26
<212> TYPE: DNA
<213> ORGANISM: Mouse

<400> SEQUENCE: 9
ctcggaatac agcatgccct ccacgc                                       26
```